United States Patent
Gran et al.

(10) Patent No.: US 11,911,210 B2
(45) Date of Patent: Feb. 27, 2024

(54) COMBINATION ULTRASOUND / OPTICAL IMAGE FOR AN IMAGE-GUIDED PROCEDURE

(71) Applicant: B-K Medical Aps, Herlev (DK)

(72) Inventors: Fredrik Gran, Limhamn (SE);
Svetoslav Ivanov Nikolov, Farum (DK)

(73) Assignee: BK MEDICAL APS, Herlev (DK)

( * ) Notice: Subject to any disclaimer, the term of this patent is extended or adjusted under 35 U.S.C. 154(b) by 862 days.

(21) Appl. No.: 16/009,631

(22) Filed: Jun. 15, 2018

(65) Prior Publication Data

US 2019/0380786 A1    Dec. 19, 2019

(51) Int. Cl.
| | | |
|---|---|---|
| *A61B 34/20* | (2016.01) | |
| *A61B 1/313* | (2006.01) | |
| *A61B 8/08* | (2006.01) | |
| *A61B 8/00* | (2006.01) | |
| *G06T 17/00* | (2006.01) | |

(Continued)

(52) U.S. Cl.
CPC ............... *A61B 8/085* (2013.01); *A61B 1/06* (2013.01); *A61B 1/313* (2013.01); *A61B 8/466* (2013.01); *A61B 8/483* (2013.01); *A61B 8/5261* (2013.01); *A61B 34/20* (2016.02); *G06T 17/00* (2013.01); *A61B 2034/2057* (2016.02); *A61B 2034/2063* (2016.02); *A61B 2034/2065* (2016.02); *A61B 2090/367* (2016.02); *A61B 2090/373* (2016.02); *A61B 2090/378* (2016.02); *G06T 2210/41* (2013.01)

(58) Field of Classification Search
CPC ......... A61B 34/20; A61B 90/00; A61B 8/466; A61B 1/045; A61B 1/06
See application file for complete search history.

(56) References Cited

U.S. PATENT DOCUMENTS 7,835,785 B2    11/2010    Scully et al.
8,556,815 B2    10/2013    Pelissier et al.
(Continued)

OTHER PUBLICATIONS

Demene, C., Spatiotemporal Clutter Filtering of Ultrafast Ultrasound Data Highly Increases Doppler and fUltrasound Sensitivity, IEEE Trans. on Medical Imaging, vol. 34, No. 11, Nov. 2015.
(Continued)

*Primary Examiner* — Boniface Ngathi
*Assistant Examiner* — Zainab Mohammed Aldarraji
(74) *Attorney, Agent, or Firm* — Daugherty & Del Zoppo, Co. LPA

(57) ABSTRACT

A system includes an image guidance system with a memory with computer executable instruction, a processor configured to execute the computer executable instructions, and a display. The computer executable instructions cause the processor to: receive a three-dimensional model of vasculature from an ultrasound imaging system, receive a real-time optical feed of an interior of a cavity from an optical camera-based guidance system, receive a first tracking signal indicative of a first spatial location of a probe of the ultrasound imaging system, receive a second spatial location of the optical camera-based guidance system, and overlay the optical feed with the three-dimensional model based on the first and second tracking signals. The display is configured to visually present the optical feed with the three-dimensional model overlaid thereover.

16 Claims, 3 Drawing Sheets

(51) Int. Cl.
    *A61B 1/06* (2006.01)
    *A61B 90/00* (2016.01)

(56) References Cited

U.S. PATENT DOCUMENTS

| | | | | |
|---|---|---|---|---|
| 2005/0113641 | A1* | 5/2005 | Bala | A61B 1/045 |
| | | | | 600/108 |
| 2010/0298712 | A1 | 2/2010 | Pelissier et al. | |
| 2011/0306025 | A1 | 12/2011 | Sheehan et al. | |
| 2014/0350404 | A1* | 11/2014 | Rajguru | A61B 8/5207 |
| | | | | 600/443 |
| 2015/0294497 | A1* | 10/2015 | Ng | A61B 8/466 |
| | | | | 382/128 |
| 2017/0007350 | A1* | 1/2017 | Popovic | A61B 34/10 |

OTHER PUBLICATIONS

Franz et al., Electromagnetic Tracking in Medicine—A Review of Technology, Validation, and Applications, IEEE Trans. on Medical Imaging vol. 33, No. 8, Aug. 2014.

Torp, Clutter Rejection Filters in Color Flow Imaging: A Theoretical Approach, IEEE Trans. on Ultrasonics, Ferroelectrics, and Frequency, vol. 44, No. 2, Mar. 1997.

Birkfellner W., et al., Tracking Devices. In: Peters T., Cleary K. (eds) Image-Guided Interventions. Springer Boston, MA 2008.

Birkeland, et al. Doppler-based 3D Blood Flow Imaging and Visualization, In SCCG 2013—29th Proceedings Spring Conference on Computer Graphics, pp. 128-135; May 2013. ISBN: 978-80-223-3377-1.

Fisherman et al., "Volume Rendering versus Maximum Intensity Projection in CT Angiography: What Works Best, When, and Why," Radiographics, vol. 26, No. 3, pp. 905-922, 2006.

P.Y. Yang, et al., "Prenatal Diagnosis of Persistent Right Umbilical Vein Using Three-Dimensioanl Sonography with Power Doppler," Taiwanese J Obstet Gynecol, Mar. 2007—vol. 46 No. 1.

Treece et al, "Regularized marching tetrahedra: Improved isosurface extraction," Comput. Graph., vol. 23, No. 4, pp. 583-598, 1999.

Treece et al., "Fast surface and vol. estimation from non-parallel cross-sections, for freehand three-dimensional ultrasound," Med. Image Anal., vol. 3, No. 2, pp. 141-173, 1999.

Treece et al., "Surface interpolation from sparse cross sections using region correspondence," IEEE Trans. Med. Imaging, vol. 19, No. 11, pp. 1106-1114, 2000.

* cited by examiner

COMBINATION ULTRASOUND / OPTICAL IMAGE FOR AN IMAGE-GUIDED PROCEDURE

TECHNICAL FIELD

The following generally relates to image guidance and more particularly to a combination ultrasound/optical image for an image guided procedure.

BACKGROUND

An image-guided procedure includes a procedure within a cavity of an object where the clinician cannot see into the cavity through the object and instead uses a displayed image of the inside of the cavity as a guide to maneuver and employ an instrument in the cavity. In one example, this includes a surgeon operating an optical camera-based guidance system while performing the procedure. The procedure could be a resection, cauterization, cryotherapy, biopsy, ablation, etc. The optical camera-based guidance system can be a laparoscope in laparoscopy, a microscope in neuro surgery, an optical interface of a surgical robot, etc.

With such a procedure, the surgeon can only see the surface of the tissue to be treated and not the tissue below the surface of the tissue to be treated. In order to avoid inadvertently damaging other tissue, e.g., cutting a vessel just below the surface of the tissue being treated, the surgeon has relied on a pre-operative image (e.g., computed tomography (CT) or magnetic resonance (MRI)) and/or a real-time image (e.g., ultrasound (US)). Unfortunately, a pre-operative image is limited in that it does not represent a current state of the tissue, which may have shifted or deformed since the imaging, and it is difficult to concurrently treat the tissue while scanning with the ultrasound probe.

SUMMARY

Aspects of the application address the above matters, and others.

In one aspect, a system includes an image guidance system with a memory with computer executable instruction, a processor configured to execute the computer executable instructions, and a display. The computer executable instructions cause the processor to: receive a three-dimensional model of vasculature from an ultrasound imaging system, receive a real-time optical feed of an interior of a cavity from an optical camera-based guidance system, receive a first tracking signal indicative of a first spatial location of a probe of the ultrasound imaging system, receive a second spatial location of the optical camera-based guidance system, and overlay the optical feed with the three-dimensional model based on the first and second tracking signals. The display is configured to visually present the optical feed with the three-dimensional model overlaid thereover.

In another aspect, a method includes receiving a three-dimensional model of vasculature from an ultrasound imaging system. The method further includes receiving a real-time optical feed of an interior of a cavity from an optical camera-based guidance system. The method further includes receiving a first tracking signal indicative of a first spatial location of a probe of the ultrasound imaging system. The method further includes receiving a second spatial location of the optical camera-based guidance system. The method further includes overlaying the optical feed with the three-dimensional model based on the first and second tracking signals. The method further includes displaying the optical feed with the three-dimensional model overlaid thereover.

In another aspect, a computer readable medium is encoded with computer executable instructions. The computer executable instructions, when executed by a processor of a computer, cause the processor to: receive a three-dimensional model of vasculature from an ultrasound imaging system, receive a real-time optical feed of an interior of a cavity from an optical camera-based guidance system, receive a first tracking signal indicative of a first spatial location of a probe of the ultrasound imaging system, receive a second spatial location of the optical camera-based guidance system, overlay the optical feed with the three-dimensional model based on the first and second tracking signals, and display the optical feed with the three-dimensional model overlaid thereover.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following general describes an approach to visualizing vasculature during an image-guided procedure of tissue. In one instance, this includes sweeping an array of an ultrasound transducer over the tissue while acquiring at least flow data (e.g., color flow mode (CFM), Doppler, etc.), creating a three-dimensional (3-D) volume with the scanned image plains, segmenting vasculature from the 3-D volume based on the flow data to create a 3-D model of the vasculature, and displaying the 3-D model overlaid over an optical image of an optical camera-based guidance system while performing the procedure. The 3-D model, in one instance, provides image-guidance on location of vasculature so that the surgeon can avoid/minimize damaging the vasculature.

Figure 1:
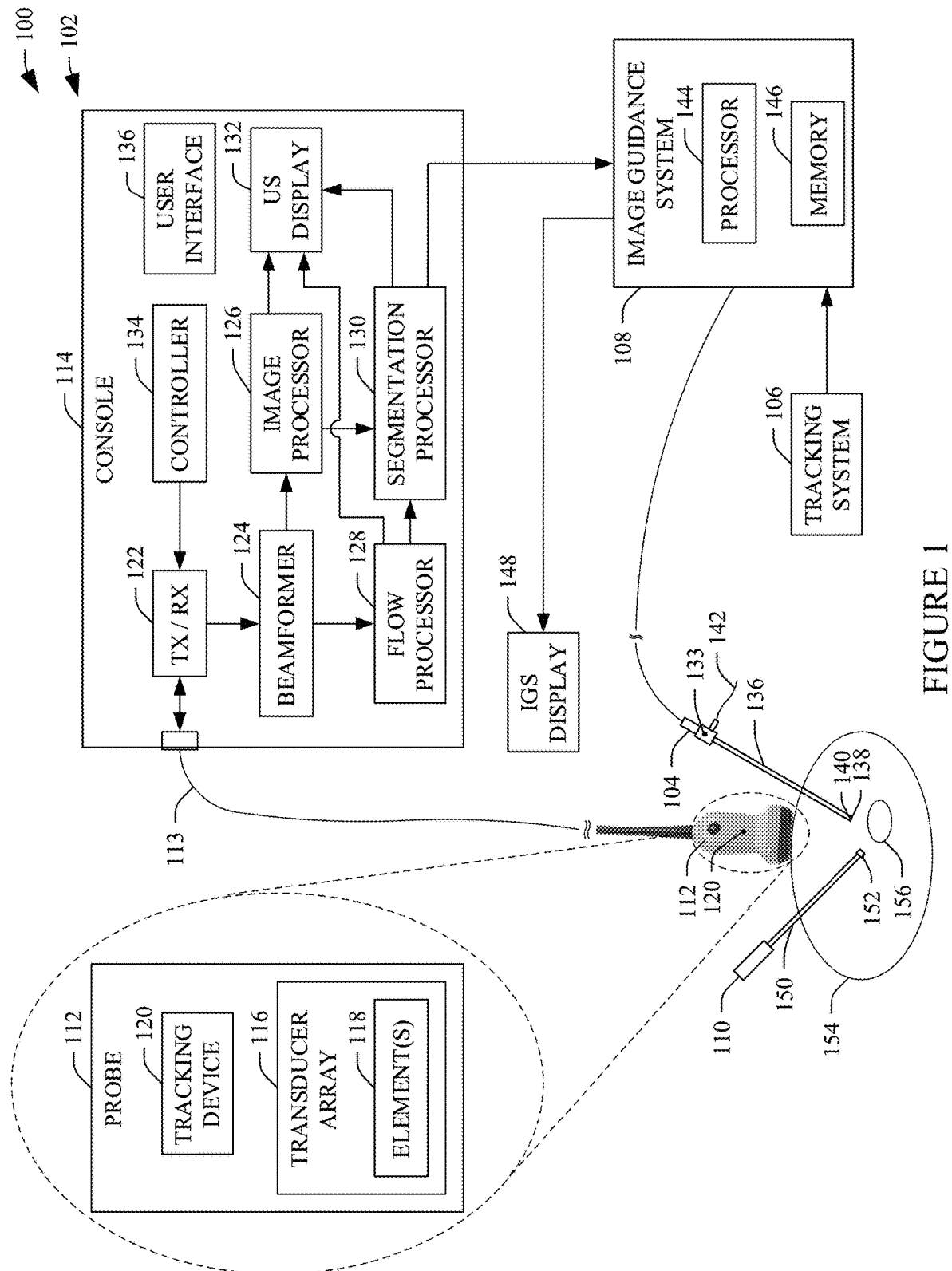
FIG. 1 schematically illustrates an example ultrasound system with a color flow mapping processor.

FIG. 1 illustrates a system 100 including ultrasound imaging system 102, an optical camera-based guidance system 104, a tracking system 106, an image-guidance system 108, and at least one instrument 110 configured for resection, cauterization, cryotherapy, biopsy, ablation, etc.

The ultrasound imaging system 102 includes a probe 112 and an ultrasound console 114, which interface through suitable complementary hardware (e.g., a cable 113, as shown) and/or wireless interfaces. The probe 112 includes a transducer array 116 with one or more transducer elements 118. The transducer array 116 can be one- or two-dimensional, linear, curved, and/or otherwise shaped, fully populated, sparse and/or a combination thereof, etc. In one instance, the transducer array 116 is configured to mechanically and/or electrically rotate to capture 3-D data.

The one or more transducer elements 118 are configured to convert an excitation electrical signal to an ultrasound pressure field. The one or more transducer elements 118 are also configured to convert a received ultrasound pressure field (an echo) into an electrical (e.g., analog radio frequency, RF) signal. The ultrasound pressure field, in one instance, is produced in response to a transmitted ultrasound pressure field interacting with structure, such as blood cells flowing in a portion of a vessel and/or other tissue, and/or other tissue.

The probe 112 further includes a probe tracking device 120, which include one or more tracking elements. One or more of the tracking elements can be external to the device 120 and/or one or more of the tracking elements can be internal to the device 120. In one instance, the one or more of the tracking elements include one or more of an emitter, a transmitter, and/or a passive sensor. Examples of such tracking devices include an electro-magnetic tracking device, an optical tracking device, an inertial tracking device, and/or other tracking device. Tracking devices are discussed in Birkfellner et al., "Tracking Devices," In: Peters T., Cleary K. (eds) Image-Guided Interventions. Springer, Boston, MA, 2008.

Transmit and receive circuitry (TX/RX) 122 is configured to generate the excitation signal conveyed to the transducer array 116 for at least flow imaging, including 3-D imaging by manual and/or electrical-mechanical sweeping of the transducer array 116. The TX/RX 122 is also configured to process the electrical signal corresponding to the received echo signal. The TX/RX 122, in one instance, is further configured to pre-condition and/or pre-process the signal (e.g., amplify, digitize, etc.). Other processing is also contemplated herein.

The illustrated embodiment shows the transmit and receive operations are performed by the same circuitry, the TX/RX 122. In a variation, the transmit and receive operations are performed by separate circuitry, e.g., transmit circuitry for transmit operations and separate receive circuitry for receive operations. One or more switches and/or other device(s) can be used to switch between transmit and receive operations and/or transmit and receive circuitry by electrically connecting and electrically disconnecting transmit and receive circuitry.

A beamformer 124 beamforms the signal, e.g., via delay-and-sum beamforming and/or other beamforming. The beamformer 124 outputs the beamformed data. An image processor 126 processes the beamformed data. For B-mode imaging, this includes generating a sequence of focused, coherent echo samples along focused scanlines of a scan-plane. The image processor 126 can also be configured to generate an A-mode, C-mode, and/or other ultrasound imaging mode image.

A flow processor 128 processes the beamformed data and generates flow images. Suitable flow processing includes color flow, Doppler and/or other flow processing. Generally, color flow is an enhanced form of Doppler that uses color to highlight the direction of blood flow. In some embodiments, the flow processor 128 is also configured to detect presence of flow (i.e. flow or no flow per voxel), e.g., using high pass filtering, singular value decomposition, principal component analysis, spatial coherence factors, etc.

Example approaches are discussed in Birkeland, et al., "Doppler-based 3D Blood Flow Imaging and Visualization," Proceeding SCCG '13 Proceedings of the 29th Spring Conference on Computer Graphics, Pages 115-122, May 1-3, 2013, Torp, "Clutter Rejection Filters in Color Flow Imaging: A Theoretical Approach," IEEE Transactions on Ultrasonics, Ferroelectrics, and Frequency Control, Vol. 44, No. 2, March 1997, and Demene et al., "Spatiotemporal Clutter Filtering of Ultrafast Ultrasound Data Highly Increases Doppler and fUltrasound Sensitivity," IEEE Transactions on Medical Imaging, Vol. 34, No. 11, November 2015.

A segmentation processor 130 is configured to segment the beamformed data based on the flow data. For example, in one instance, the segmentation processor 130, for each scan plane, distinguishes flow from surrounding tissue, and generates 3-D model representing vasculature tissue (i.e. blood vessels). In one instance, this includes comparing the data in each scan plane to a predetermined threshold and classifying regions satisfying the predetermined threshold as flow data and classifying other regions as non-flow data. The regions classified as flow data is then segmented and used to generate the 3-D model. In some embodiments, the segmentation processor 130 utilizes the B-mode images to refine the 3-D model, e.g., at border the between the vasculature tissue and the surrounding tissue.

Figure 2:
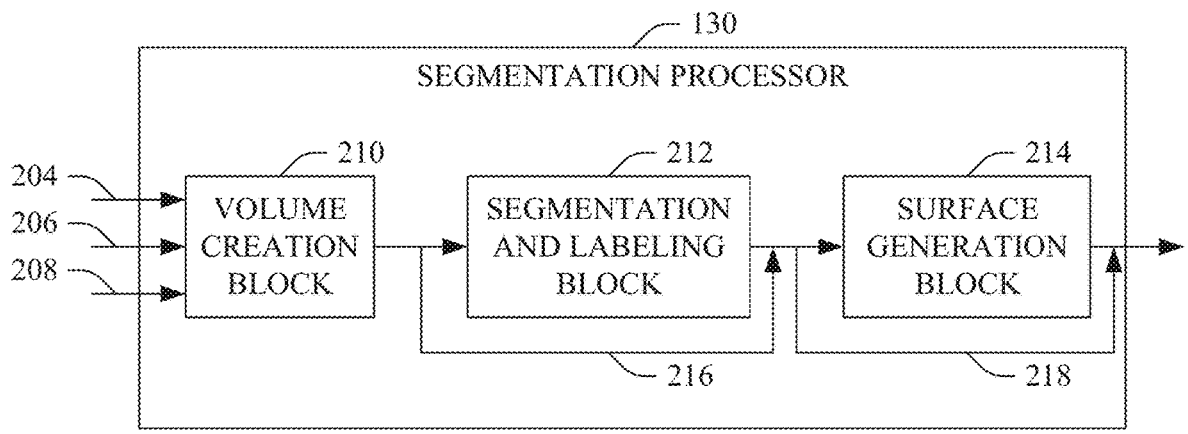
FIG. 2 schematically illustrates a non-limiting examples of the segmentation processor of the ultrasound system.

FIG. 2 schematically illustrates a non-limiting example of the segmentation processor 130. Inputs to the segmentation processor 130 include tracking data 204, a flow image 206, and a tissue-flow mask 208. The tracking data 204 come from the tracking device 120 and tracking system 106. The flow image 206 and the tissue-flow mask 208 are produced by the flow processor 128. The flow image 206 can be a color-flow image or a power doppler image. The tissue-flow mask 208 can be a separate data stream or incorporated in the flow image 206. The tissue flow-mask consists typically of values between 0 and 1 indicating the probability that a given pixel of the flow image is true blood flow (value of 1) or not (value of 0).

Figure 3:
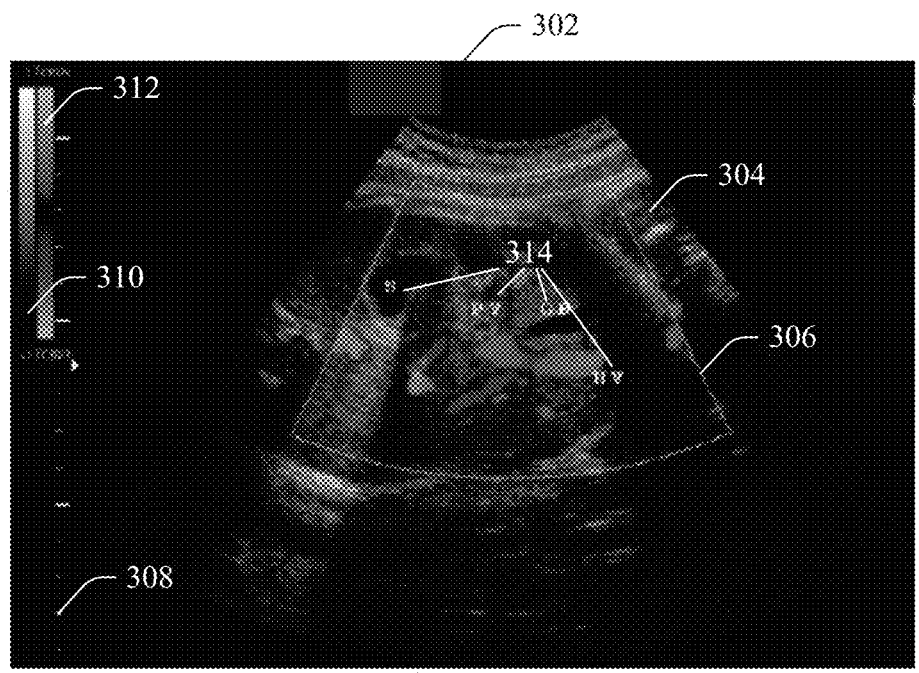
FIG. 3 shows an example color flow image.
Figure 4:
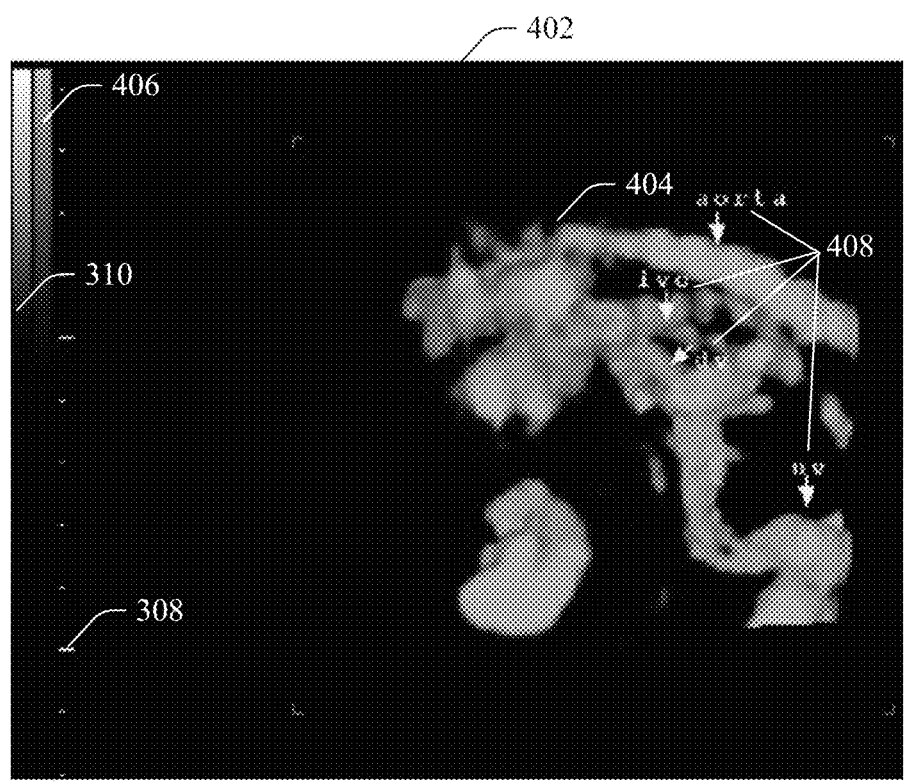
FIG. 4 shows an example Power-Doppler image.

Briefly turning to FIGS. 3 and 4, examples of a color flow image and a power doppler image are shown. FIG. 3 shows a 2D ultrasound image 302 consisting of a B-mode image 304 overlaid with a color flow image 306. The display also includes a standard depth axis 308 and color-bars 310 and 312 for the B-mode image 304 and the color flow image 306, respectively. FIG. 3 further shows labels 314 for predetermined anatomical structures, which in the illustrated case are: umbilical vein (UV), stomach (S), portal vein (PV), and gallbladder. FIG. 4 shows a screen-shot 402 consisting of a 3D-rendered Power-Doppler image 404, the depth axis 308, the color-bar 310 for the B-mode image, and a color bar 406 for the Power-Doppler image 404. The overlay includes labels 408 for predetermined anatomical structures, which in this case are: aorta; inferior vena cava (ivc); ductus venosus (dv); and umbilical vein (uv). The user can rotate, translate and zoom the vessels rendered in 3D.

Returning to FIG. 2, The flow image 206 and the tissue-flow mask 208 can be 2D planar images, or 3D volumetric scans, depending on the probe 112. In all cases, the tracking data 204 include coordinates and orientation of the origin of the images. The volume creation block 210 maps the flow image 206 to a volumetric image. The created volume can be displayed directly to the user by the US display 132 by employing techniques such as volume rendering or maximum intensity projection. An example of this is discussed in Fishman et al., "Volume Rendering versus Maximum Intensity Projection in CT Angiography: What Works Best, When, and Why," Radiographics, vol. 26, no. 3, pp. 905-922, 2006. In this case, the blocks 212 and 214 are bypassed by employing data paths 216 and 218.

The segmentation and labeling block 212 clusters the voxels that belong to the same vessel and assigns them labels. An example of this is described in Bradski et al., "Learning OpenCV. Computer Vision with the OpenCV Library", ISBN 9780596156022, O'Reilly Media, 2008. The output of the segmentation and labeling block 212 can be sent to the US display 132. The surface generation block 214 uses the labeled voxel data to create triangle meshes of the surface of the vessel walls. Examples of suitable approaches are discussed in Treece et al, "Regularized marching tetrahedra: Improved iso-surface extraction," Comput. Graph., vol. 23, no. 4, pp. 583-598, 1999, Treece et al., "Fast surface and volume estimation from non-parallel cross-sections, for freehand three-dimensional ultrasound," Med. Image Anal., vol. 3, no. 2, pp. 141-173, 1999, and Treece et al., "Surface interpolation from sparse cross sections using region correspondence," IEEE Trans. Med. Imaging, vol. 19, no. 11, pp. 1106-1114, 2000.

A display (US Display) 132 is configured to display images, e.g., B-mode, flow images, and/or the 3-D model. A controller 134 is configured to control one or more of the components of the ultrasound imaging system 100. Such control can be based on available modes of operation such as B-mode and/or flow mode, etc. A user interface 136 includes one or more input devices such as a keyboard, a trackball, a mouse, a touch sensitive screen, etc. configured to allow a user to interact with the ultrasound imaging system 102.

In this example, the optical camera-based guidance system 104 includes a laparoscope 133, which includes a shaft 136, a camera 138 disposed at a first end of the shaft 136, a light guide 140 disposed at the first end of the shaft 136, a light source 140 in optical communication with the light guide 140, and a laparoscope tracking device 142, which include one or more tracking elements. Other suitable systems include a microscope, an optical interface of a surgical robot, etc. One or more of the tracking elements can be external to the tracking device 142 and/or one or more of the tracking elements can be internal to the tracking device 142. In one instance, the one or more of the tracking elements include one or more of an emitter, a receiver, and/or a passive sensor. Examples of such tracking devices include an electro-magnetic tracking device, an optical tracking device, an inertial tracking device, and/or other tracking device. Tracking devise are discussed in Birkfellner et al.

The tracking system 106 interacts with the probe tracking device 120 and the laparoscope tracking device 142, registers their spatial coordinate systems, and determines a location and an orientation of the probe tracking device 120 and the laparoscope tracking device 142 relative to each other. For example, where the probe tracking device 120 and/or the laparoscope tracking device 142 includes magnets, the tracking system 106 measures a magnetic field strength of the magnets, which depends on a distance and direction of the magnets to the tracking system 106, and the strength and direction is used to determine location and orientation. In another example, where the probe tracking device 120 and/or the laparoscope tracking device 142 includes external optical elements, the tracking system 106 includes an optical device such as a video camera the records the spatial orientation of the optical elements to determine location and orientation.

Examples of suitable tracking system 106 are described in U.S. patent application US 2010/0298712 A1, filed Feb. 10, 2010, and entitled "Ultrasound Systems Incorporating Position Sensors and Associated Method," and U.S. Pat. No. 8,556,815 B2, filed May 6, 2010, and entitled "Freehand Ultrasound Imaging Systems and Methods for Guiding Elongate Instruments," both of which are incorporated herein by reference in their entireties. Another example is discussed in U.S. Pat. No. 7,835,785 B2, filed Oct. 4, 2005, and entitled "DC Magnetic-Based Position and Orientation Monitoring system for Tracking Medical Instruments." Other tracking systems are discussed in Birkfellner et al. Other approaches are also contemplated herein.

The image guidance system 108 includes at least a processor 144 (e.g., a central processing unit, a microprocessor, etc.) and memory 146 (e.g., physical memory, etc.). The image guidance system 108 receives the 3-D model from the console 114 of the ultrasound imaging system 102, the optical signal/feed from the optical camera-based guidance system 104, and the tracking signal from the tracking system 106, and displays, via a display (IGS Display) 148, the optical signal/feed from the optical camera-based guidance system 104 overlaid with the 3-D model based on the tracking signal. In one instance, the memory 146 include an augmented reality algorithm, the processor 144 executes the augmented reality algorithm to combine the optical signal/feed and the 3-D model. Other approaches are also contemplated herein. Depth information can be added through shading, fading, intensity, color, etc.

The at least one instrument 110 includes a shaft 150 and a device 152 disposed at a first end of the shaft 150. The device 152 can include a suitable device for resection, cauterization, cryotherapy, biopsy, ablation, etc. For example, the device 152 can include a grasper, scissors, a stapler, etc.

The probe 112 of the ultrasound imaging system 102, the optical camera-based guidance system 104, and the at least one instrument 110 are shown in connection with an object 154 and material of interest 156 within the object 154. Where the object 154 is a patient, a portal such as a trocar or the like may first be placed through the wall of the object 154 and the optical camera-based guidance system 104 and the at least one instrument 110 are inserted into cannulas of the trocars and into the cavity of the object 154.

Figure 5:
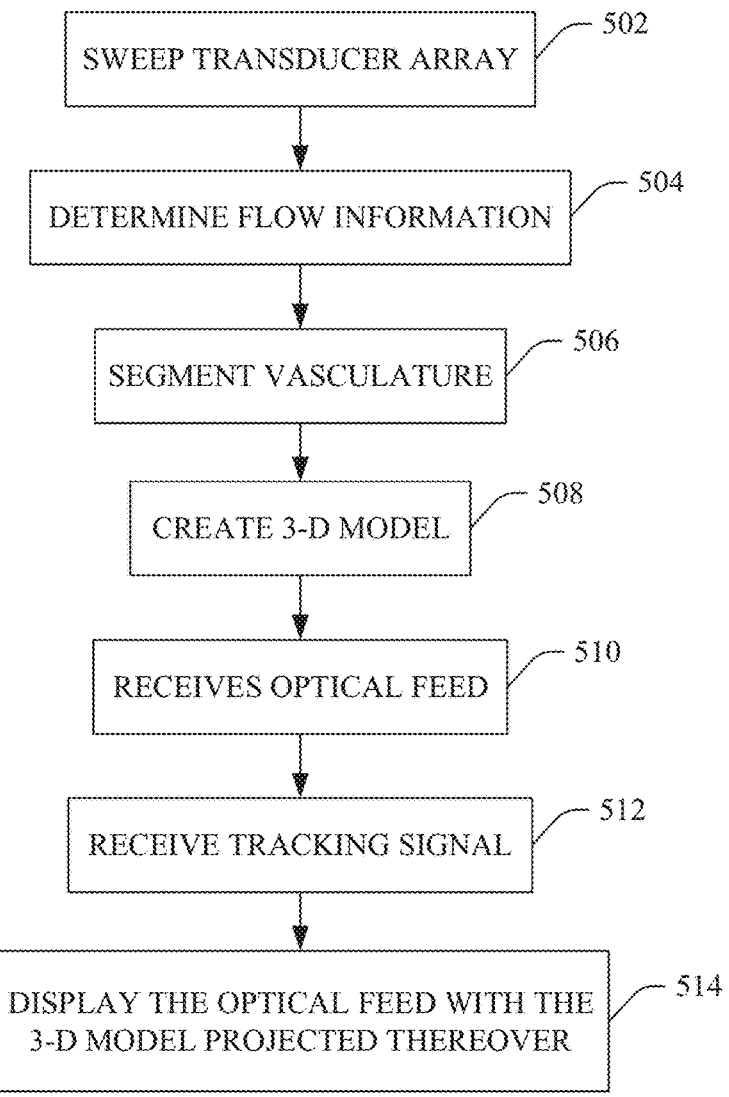
FIG. 5 illustrates an example method in accordance with an embodiment herein.

FIG. 5 illustrates an example method in accordance with an embodiment herein.

It is to be understood that the following acts are provided for explanatory purposes and are not limiting. As such, one or more of the acts may be omitted, one or more acts may be added, one or more acts may occur in a different order (including simultaneously with another act), etc.

At 502, the transducer array 116 is swept over the material of interest 156.

At 504, the flow processor 128 determined flow information from the acquired data.

At 506, the segmentation processor 130 segments vasculature from the acquired data with the flow information.

At 508, the segmentation processor 130 creates the 3-D model of the vasculature with the segmentation.

At 510, the image guidance system 108 receives an optical feed from the optical camera-based guidance system 104.

At 512, the image guidance system 108 receives the tracking signal from the tracking system 106.

At 514, the image guidance system 108 displays the optical feed with the 3-D model projected thereon based on the tracking signal, which aligns their coordinate systems.

This process can be repeated one or more times during the procedure and/or after the procedure, e.g., to validate vasculature was avoided.

The 3-D model can be static and outline the average contours of the vasculature or dynamic and show pulsation of the flow.

Depth information can be added through shading, fading, intensity, color, etc. The user utilizes the displayed information to guide the instrument 110 to the material of interest 156 and treat the material of interest 156 with the instrument 110.

The above may be implemented by way of computer readable instructions, encoded or embedded on computer readable storage medium (which excludes transitory medium), which, when executed by a computer processor(s) (e.g., central processing unit (CPU), microprocessor, etc.), cause the processor(s) to carry out acts described herein. Additionally, or alternatively, at least one of the computer readable instructions is carried by a signal, carrier wave or other transitory medium, which is not computer readable storage medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A system, comprising:
   a probe, including:
      a transducer array configured to acquire three-dimensional data of a vasculature; and
      a tracking device configured to produce a first tracking signal indicative of a first spatial location of the probe;
   a beamformer configured to beamform the acquired data;
   an image processor configured to produce B-mode images from the beamformed data;
   a flow processor configured to produce flow images from the beamformed data and to produce a tissue-flow mask from the beamformed data, wherein the tissue flow-mask consists of values from 0 to 1, indicating a probability that a given pixel of the flow image is blood flow, where a value of 1 indicates a voxel is blood flow, a value of 0 indicates the voxel is not blood flow, and a value between 0 and 1 indicates whether the voxel more likely is not blood or is blood;
   a segmentation processor configured to:
      map the flow images to create a volume;
      identify voxels of the volume belonging to a vessel based on the tissue-flow mask; and
      extract a surface of a wall of the blood vessel to create a three-dimensional model of the blood vessel;
   an image guidance system, including:
      a memory with computer executable instructions;
      a processor configured to execute the computer executable instructions, which causes the processor to:
         receive the three-dimensional model of vasculature from the ultrasound imaging system;
         receive a real-time optical feed of an interior of a cavity from an optical camera-based guidance system;
         receive the first tracking signal;
         receive a second tracking signal indicative of a second spatial location of the optical camera-based guidance system; and
         overlay the optical feed with the three-dimensional model based on the first and second spatial locations; and
      a display configured to visually present the optical feed with the three-dimensional model overlaid thereover, wherein the three-dimensional model is a static model that outlines average contours of the vasculature.

2. The system of claim 1, wherein the tissue-flow mask and the flow images are separate images.

3. The system of claim 1, wherein the image processor is further configured to produce B-mode images from the beamformed data and the segmentation processor refines the three-dimensional model with the B-mode images.

4. The system of claim 1, wherein the tissue-flow mask is incorporated into the flow images.

5. The system of claim 1, wherein the optical camera-based guidance system comprises:
   a shaft with a first end and a second opposing end;
   a light guide disposed at the first end;
   an optical device disposed at the first end;
   a light source in optical communication with the light guide; and
   an optical path from the optical device to the processor, wherein the optical path routes an optical feed from the optical device to the processor, which processes the optical feed.

6. The system of claim 5, further comprising:
   a tracking device of the optical camera-based guidance system; and
   a tracking system configured to interact with the tracking device to produce the second tracking signal.

7. The system of claim 1, wherein the optical feed shows a location of an instrument in the cavity.

8. The system of claim 1, wherein the three-dimensional model shows vasculature behind an outer surface tissue being treated by an instrument in the cavity.

9. A method, comprising:
   producing flow images from beamformed data;
   producing a tissue-flow mask from the beamformed data, wherein the tissue flow-mask consists of values from 0 to 1, indicating a probability that a given pixel of the flow image is blood flow, where a value of 1 indicates a voxel is blood flow, a value of 0 indicates the voxel is not blood flow, and a value between 0 and 1 indicates whether the voxel more likely is not blood or is blood;
   mapping the flow images to create a volume;
   identifying voxels of the volume belonging to a vessel based on the tissue-flow mask;
   extracting a surface of a wall of the vessel to create a three-dimensional model of the vessel;
   receiving a real-time optical feed of an interior of a cavity from an optical camera-based guidance system;
   receiving a first tracking signal indicative of a first spatial location of a probe of the ultrasound imaging system;
   receiving a second tracking signal indicative of a second spatial location of the optical camera-based guidance system; and
   overlaying the optical feed with the three-dimensional model based on the first and second spatial locations; and
   displaying the optical feed with the three-dimensional model overlaid thereover,
   wherein the three-dimensional model is a dynamic model that visually presents pulsation of the flow.

10. The method of claim 9, further comprising:
    acquiring three-dimensional data of the vasculature;
    beamforming the acquired data;
    producing flow data from the beamformed data; and
    segmenting the three-dimensional model from the flow data.

11. The method of claim 9, wherein the optical feed shows a location of an instrument in the cavity, and the three-dimensional model shows vasculature behind an outer surface tissue being treated by the instrument in the cavity.

12. A computer readable medium encoded with computer executable instructions which when executed by a processor of a computer causes the processor to:
  produce flow images from beamformed data;
  produce a tissue-flow mask from the beamformed data, wherein the tissue flow-mask consists of values from 0 to 1, indicating a probability that a given pixel of the flow image is blood flow, where a value of 1 indicates a voxel is blood flow, a value of 0 indicates the voxel is not blood flow, and a value between 0 and 1 indicates whether the voxel more likely is not blood or is blood;
  map the flow images to create a volume;
  identify voxels of the volume belonging to a vessel based on the tissue-flow mask;
  extract a surface of a wall of identified vessel to create the three-dimensional model of the blood vessel;
  receive a real-time optical feed of an interior of a cavity from an optical camera-based guidance system;
  receive a first tracking signal indicative of a first spatial location of a probe of the ultrasound imaging system;
  receive a second tracking signal indicative of a second spatial location of the optical camera-based guidance system;
  overlay the optical feed with the three-dimensional model based on the first and second spatial locations; and
  display the optical feed with the three-dimensional model overlaid thereover, wherein the three-dimensional model outlines average contours of the vasculature or visually presents pulsation of the flow.

13. The computer readable medium of claim 12, wherein the three-dimensional model is a static model.

14. The computer readable medium of claim 12, wherein the three-dimensional model is a dynamic model.

15. The computer readable medium of claim 12, wherein the optical feed shows a location of an instrument in the cavity.

16. The computer readable medium of claim 12, wherein the three-dimensional model shows vasculature behind an outer surface tissue being treated by the instrument in the cavity.

* * * * *